United States Patent [19]

Howard

[11] Patent Number: 5,350,747
[45] Date of Patent: Sep. 27, 1994

[54] HETEROARYL PIPERAZINE ANTIPSYCHOTIC AGENTS

[75] Inventor: Harry R. Howard, Bristol, Conn.

[73] Assignee: Pfizer Inc, New York, N.Y.

[21] Appl. No.: 836,019

[22] PCT Filed: Jul. 7, 1989

[86] PCT No.: PCT/US89/02954

§ 371 Date: Feb. 20, 1992

§ 102(e) Date: Feb. 20, 1992

[87] PCT Pub. No.: WO91/00863

PCT Pub. Date: Jan. 24, 1991

[51] Int. Cl.[5] .................... A61K 31/55; C07D 417/14
[52] U.S. Cl. .................... 514/213; 544/121; 544/363; 544/364; 514/255; 514/235.2; 540/523
[58] Field of Search ............... 540/523; 544/363, 364, 544/121; 514/213, 255, 235.2

[56] References Cited

U.S. PATENT DOCUMENTS 4,818,755 4/1989 Kuhla et al. .................... 514/228.2

OTHER PUBLICATIONS

I-560.5 Indoline, 99% [496-15-1] *Aldrich Chemical Co.* p. 726, (1992).
T1,550-4 1,2,3,4-Tetrahydroquinoline, 98% [635-46-1], *Aldrich Chemical Co.* p. 1166, (1992).
B. D. Astill & V. Boekelheide: "The Synthesis of 1-benzazepine Derivatives as Model Compounds Related to APO-$\beta$-Erythroidine[1,2]", 77, *Journal of Medicinal Chemistry* pp. 4079–4083 (1955).
G. Coudert. G. Guillaumet. B. Loubinoux: "A New Synthesis of 3,4-Dihydro-2H-1,4-benzoxazines using Solid-Liquid Phase-Transfer Catalysis", 39 *Synthesis*, 514–543 (1979).
Richard M. Forbis and Kenneth L. Rinehart, Jr.: "Nybomycin. Vii. preparative Routes to Nybomycin and Deoxynybomycin[1,2]", *Journal of Medicinal Chemistry*, 5003–5013 (1973).
Rogert Brettle and Sa'ad M. Shibib: "Selective Reduction of $\alpha\beta$-Olefinic Amides and Lactams by Magnesium and Methanol", *J.C.S. Perkin Tran I*, 2912–2919 (1981).

*Primary Examiner*—Robert T. Bond
*Attorney, Agent, or Firm*—Peter C. Richardson; Paul Ginsburg; Garth Butterfield

[57] ABSTRACT

Compounds of the formula

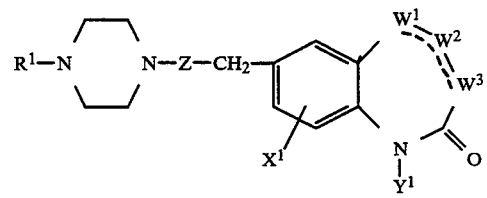

and pharmaceutical compositions comprising them, wherein $R^1$, Z, X, W and Y are as defined below. The compounds are useful in the treatment of psychosis and anxiety.

6 Claims, No Drawings

HETEROARYL PIPERAZINE ANTIPSYCHOTIC AGENTS

BACKGROUND OF THE INVENTION

The present invention is directed to novel heteroaryl piperazine compounds of the formula I, depicted below, which exhibit neuroleptic activity and are useful in the treatment of psychosis and anxiety.

Other compounds useful in treating psychotic disorders are known. For example, European Patent Application 0281309 states that compounds of the formula

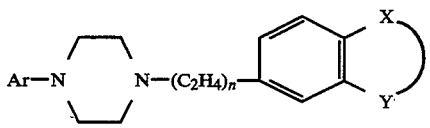

wherein Ar, n, X and Y are as defined in that application, are useful in treating psychotic disorders. The novel compounds of the present invention, however, exhibit substantially greater neuroleptic activity than such known compounds.

SUMMARY OF THE INVENTION

The present invention relates to compounds of the formula

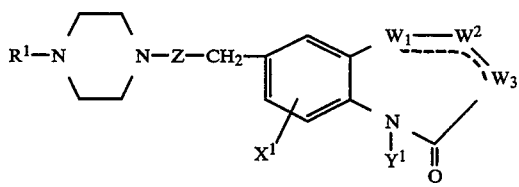

wherein $W^1$ is $CR^2R^3$, $W^2$ is $CR^4R^5$, $W^3$ is $CR^6R^7$ and one of $W^1$, $W^2$ and $W^3$ may be absent and wherein the broken line extending from $W^1$ to $W^3$ represents an optional double bond between either and $W^1$ and $W^2$ or $W^2$ and $W^3$, in which case two of $R^2$, $R^3$, $R^4$, $R^5$, $R^6$ and $R^7$ are absent; and wherein $X^1$ is hydrogen, halogen, $(C_1-C_4)$-alkyl, $(C_1-C_4)$alkoxy, nitro, cyano, trifluoromethyl, or pentafluoroethyl or $X^1$ forms a heterocyclic ring with $Y^1$; $Y^1$ is hydrogen, $(C_1-C_4)$ alkyl, phenyl or substituted phenyl, wherein said substituted phenyl is substituted with one or more substituents that are independently selected from the group consisting of halogen, $(C_1-C_4)$ alkyl, nitro, cyano, $(C_1-C_4)$ alkoxy, trifluoromethyl or pentafluoroethyl, or $Y^1$ forms a heterocyclic ring with $X^1$;

$R^1$ is

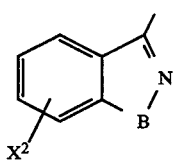

wherein B is selected from the group consisting of S, O and $NY^2$; $X^2$ is hydrogen, halogen, $(C_1-C_4)$ alkyl, $(C_1-C_4)$ alkoxy nitro cyano trifluoromethyl or pentafluoroethyl, or $X^2$ forms a heterocyclic ring with $Y^2$; $Y^2$ is hydrogen, $(C_1-C_4)$ alkyl, phenyl or substituted phenyl, wherein said substituted phenyl is substituted with one or more substituents that are independently selected from the group consisting of halogen, $(C_1-C_4)$ alkyl, $(C_1-C_4)$ alkoxy, nitro, cyano, trifluoromethyl or pentafluoro ethyl, or $Y^2$ forms a heterocyclic ring with $X^2$, $R^2$, $R^3$, $R^4$, $R^5$, $R^6$ and $R^7$ are independently selected from the group consisting of hydrogen and lower alkyl or any two of $R^2$, $R^3$, $R^4$, $R^5$, $R^6$ and $R^7$ taken together with the carbon or carbons to which they are attached form a $(C_3-C_7)$ saturated or unsaturated carbocyclic ring; and Z is $(C_1-C_6)$alkyl, branched $(C_1-C_6)$alkyl, $(C_1-C_6)$alkenyl or branched $(C_1-C_6)$alkenyl.

The present invention also relates to the pharmaceutically acceptable acid addition salts of the compounds of formula I. Such pharmaceutically acceptable acid addition salts include, but are not limited to the respective salts of acetic, malic, citric, fumaric, sulfuric, hydrochloric, hydrobromic, hydroiodic, sulfonic such as methanesulfonic and p-toluenesulfonic, and related acids.

Preferred compounds of the invention are:

6-(2-(4-(1,2-benzisothiazol-3-yl)piperazinyl)ethyl)-1,2,3,4-tetrahydro-2(1H)-quinolinone hydrochloride hemihydrate, 4(R,S)-methyl-6-(2-(4-(1,2-benzisothiazol-3-yl)piperazinyl)ethyl)-1,2,3,4-tetrahydro-2(1H)-quinolinone hydrochloride hydrate, 4S-methyl-6-(2-(4-(1,2-benzisothiazol-3-yl)piperazinyl)ethyl)-1,2,3,4-tetrahydro-2(1H)-quinolinone hydrochloride hydrate, 4R-methyl-6-(2-(4-(1,2-benzisothiazol-3-yl)piperazinyl)ethyl)-1,2,3,4-tetrahydro-2(1H)-quinolinone hydrochloride hydrate, 7-chloro-6-(2-(4-(1,2-benzisothiazol-3-yl)piperazinyl)ethyl)-1,2,3,4-tetrahydro-2(1H)-quinolinone quarterhydrate, 6-(3-(4-(1,2-benzisothiazol-3-yl)piperazinyl)propyl)-1,2,3,4-tetrahydro-4-methyl-2(1H)-quinolinone, 7-(2-(4-(1,2-benzisothiazol-3-yl)-piperazinyl)-ethyl)-1,3,4,5-tetrahydro-2H-1-benzazepin-2-one, 1-ethyl-6-(2-(4-(1,2-benzisothiazol-3-yl)piperazinyl)ethyl)-1,2,3,4-tetrahydro-2(1H)-quinolinone, and 4,4-dimethyl-6-(2-(4-(1,2-benzisothiazol-3-yl)-piperazinyl)ethyl)-1,2,3,4-tetrahydro(2(1H)-quinoline.

Specific compounds of the invention are:

6-(2-(4-(1,2-benzisothiazol-3-yl)piperazinyl)ethyl)-1,2,3,4-tetrahydro-7-trifluoromethyl-2(1H)-quinolinone, 7-chloro-4-methyl-6-(2-(4-(1,2-benzisothiazol-3-yl)-piperazinyl)ethyl)-1,2,3,4-tetrahydro-2(1H)-quinolinone hydrochloride hydrate, 6-(2-(4-(1,2-benzisothiazol-3-yl)piperazinyl)ethyl)-1,2,3,4-tetrahydro-4-methyl-7-trifluoromethyl-2(1H)-quinolinone, 6-(2-(4-(1,2-benzisothiazol-3-yl)piperazinyl)ethyl)-1,2,3,4-tetrahydro-3,4-dimethyl-2(1H)-quinolinone, 6-(2-(4-(1,2-benzisothiazol-3-yl)piperazinyl)ethyl)-1,2,3,4-tetrahydro-5,7-dimethyl-2(1H)-quinolinone, 6'-(2-(4-(1,2-benzisothiazol-3-yl)piperazinyl)ethyl-1',2',3',4'-tetrahydro-spiro[cyclopentane-1,4'-quinoline]-2'-one, 6'-(2-(4-(1,2-benzisothiazol-3-yl)piperazinyl)ethyl)-1',2',3',4'-tetrahydro-spiro[cyclopropane-1,4'-quinoline]-2'-one, 6-(2-(4-(6-chloro-1,2-benzisothiazol-3-yl)piperazinyl)e-
thyl)-1,2,3,4-tetrahydro-4-methyl-2(1H)-quinolinone, 6-(2-(4-(6-fluoro-1,2-benzisothiazol-3-yl)piperazinyl)e-
thyl)-1,2,3,4-tetrahydro-4-methyl-2(1H) -quinoli-
none, 6-(2-(4-(5-fluoro-1,2-benzisothiazol-3-yl)piperazinyl)e-
thyl)-1,2,3,4-tetrahydro-4-methyl-2(1H)-quinolinone, 7-(2-(4-(1,2-benzisothiazol-3-yl)piperazinyl)ethyl)-
1,3,4,5-tetrahydro-8-chloro-2H-1-benzazepin-2-one,
and 7-(2-(4-(1,2-benzisothiazol-3-yl)piperazinyl)ethyl)-
1,3,4,5-tetrahydro-5,5-dimethyl-2H-1-benzazepin-
2-one.

The compounds of formula I may have optical centers and therefore may occur in different stereochemical configurations. The invention includes all stereoisomers of such compounds of formula I, including racemic mixtures thereof.

The invention also relates to pharmaceutical compositions for administration to a human which comprise a compound of the formula I or a pharmaceutically acceptable acid addition salt thereof, and a pharmaceutically acceptable carrier. Said pharmaceutically acceptable acid addition salts include but are not limited to those listed above.

The invention further relates to a method of preventing or treating human disorders such as psychosis and anxiety, comprising administering to a person in need of such treatment or prevention a compound of formula I in an amount effective to treat or prevent such disorder.

DETAILED DESCRIPTION OF THE INVENTION

Reaction scheme 1 below illustrates the preparation of compounds of formula I. Reaction scheme 2 below illustrates two methods of preparing compounds of the formula II, the starting material depicted in scheme 1.

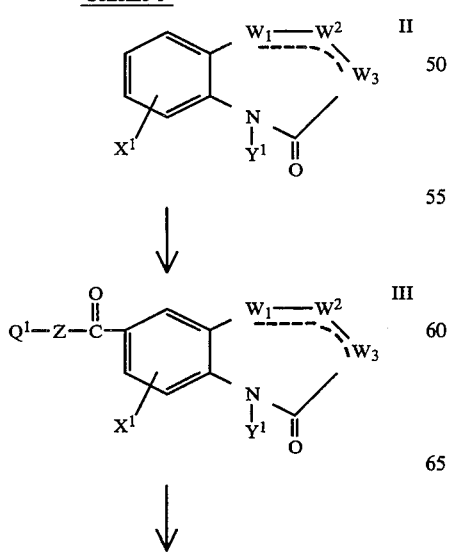

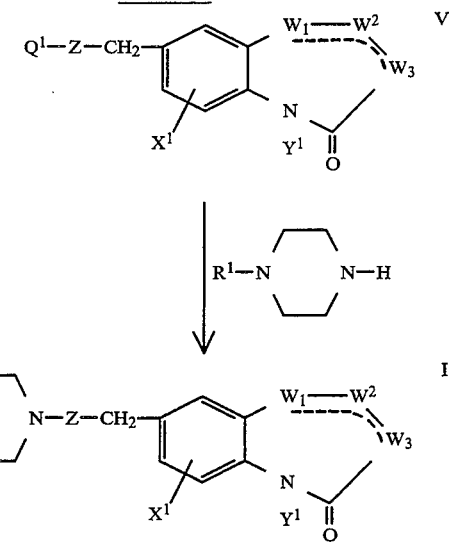

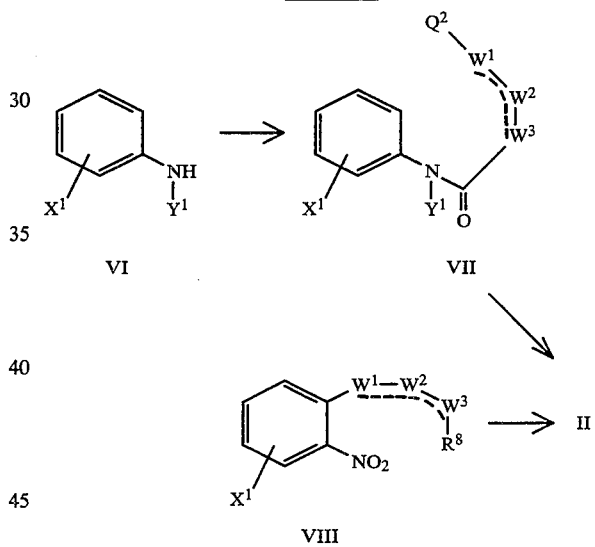

Compounds of the formula I, wherein $R^1$, $W^1$, $W^2$, $W^3$, $X^1$, $Y^1$ and Z are as defined above may be prepared by reacting piperazines of formula V, wherein $R^1$ is as defined above, with compounds of formula IV, wherein $W^1$, $W^2$, $W^3$, $X^1$, $Y^1$ and Z are as defined above and $Q^1$ is a halogen (e.g., F, Br, Cl, I) or other suitable leaving group (e.g. $CH_3SO_3$, p-toluenesulfonyl). The reaction is generally performed in a polar solvent such as a lower alcohol, dimethylformamide, dimethylacetamide, acetonitrile, or methyl isobutyl ketone, and in the presence of a weak tertiary base such as triethylamine or an inorganic base such as sodium or potassium carbonate. A catalytic amount of sodium or potassium iodide can be employed to further the degree of completion. The reaction may be conducted at a temperature within the range of about 0° C. to about 250° C., and preferably it is conducted at the reflux temperature (boiling point) of the chosen solvent.

The piperazine derivatives of the formula V may be prepared by methods known in the art and, in particular, as described by Lowe et al. in European Patent Application 0281309, in which an aryl or heteroaryl halide of the formula R-Hal (wherein Hal is F, Cl, Br, I) is reacted in an inert solvent (e.g., diglyme) at a temperature from about room temperature to about the reflux temperature of the selected solvent for about one half to about 48 hours and preferably for about 16–24 hours.

Compounds of the formula IV may be prepared from compounds of the formula III, wherein $Q^1$, $W^1$, $W^2$, $W^3$, $X^1$, $Y^1$ and Z are as defined above by methods available to those practicing in the art and analogous to those described in European Patent Application 0281309. Thus, compounds of the formula IV may be obtained by reducing a compound of the formula III with a reducing agent such as triethylsilane in trifluoroacetic acid.

Compounds of the formula III may be obtained by reacting a compound of the formula II, wherein $W^1$, $W^2$, $W^3$, $X^1$ and $y^1$ are as defined above, with a haloalkanoic acid or a haloalkanoyl halide, wherein the halogen is selected from the group consisting of F, Cl, Br and I, employing, for example, Friedel-Crafts conditions (e.g., aluminum trichloride in carbon disulfide or methylene dichloride under an inert atmosphere) or via acylation in a medium such as polyphoshoric acid at a temperature from about room temperature to about 100° C.

The preparation of the compounds of the formula II used in the above process can be accomplished by several methods, as described in the literature and outlined in scheme 2. Referring to scheme 2, an aryl amine of the formula VI, wherein $X^1$ and $Y^1$ are as defined above, can be converted, using methods known in the art, to an arylamide of the formula VII, wherein $W^1$, $W^2$, $W^3$, $X^1$, and $Y^1$ are as defined above and $Q^2$ is defined as $Q^1$ above, which may then be cyclized to produce a compound of the formula II.

Compounds of the formula II, wherein a carbon-carbon double bond exists between either $W^1$ and $W^2$ or $W^2$ and $W^3$ may be reduced using known methods such as catalytic hydrogenation or reduction with magnesium metal in methanol to produce compounds of the formula II, wherein the corresponding bond between either $W^1$ and $W^2$ or $W^2$ and $W^3$ is a carbon-carbon single bond.

Compounds of the formula II wherein $W^1$, $W^2$, $W^3$ and $X^1$ are as defined above and $Y^1$ is hydrogen, can alternatively be prepared by other known methods, as illustrated in scheme 2. For example, they can be prepared by concomitantly reducing and/or cyclizing a compound of the formula VIII, wherein $W^1$, $W^2$, $W^3$, and $X^1$ are as defined above and $R^8$ is a nitrile, a carboxylic acid or a carboxylate such as a methyl or ethyl ester. They may also be prepared from compounds of the formula IX, wherein $W^1$, $W^2$, $W^3$ and $X^1$ are as defined above, using such known methods as Schmidt or Beckmann rearrangements.

The pharmaceutically acceptable acid addition salts of the compounds of formula I are prepared in a conventional manner by treating a solution or suspension of the free base, i.e. a compound of formula I, with about one chemical equivalent of a pharmaceutically acceptable acid. Conventional concentration and recrystallization techniques are employed in isolating the salts.

The neuroleptic activity of the present compounds may be demonstrated by methods based on standard procedures. In one method, adult male Sprague-Dawley rats are pretreated with appropriate doses of the test compound by subcutaneous injection. One half hour later all rats are injected intraperitoneally with 1 mg/kg apomorphine hydrochloride dissolved in an 0.1% ascorbate solution. The rats are rated behaviorally according to the following scale at 5, 15, 25, 35 and 45 minutes after the apomorphine injection: 0=alert but not moving, 1=moving around the cage, 2=discontinuous sniffing behavior, 3=continuous sniffing with discontinuous oral movements, and 4=continuous licking and chewing movements.

The neuroleptic activity of the compounds of this invention makes them useful for treating psychotic disorders in human subjects. For example, these compounds are useful for treating psychotic disorders of the schizophrenic types and in particular the compounds are useful for removing or ameliorating such symptoms as anxiety, agition, excessive aggression, tension and social or emotional withdrawal in psychotic patients.

A neuroleptic compound of the formula I or a pharmaceutically-acceptable salt thereof can be administered to a human subject either alone or preferably in combination with pharmaceutically-acceptable carriers or diluents in a pharmaceutical composition according to standard pharmaceutical practice. A compound can be administered orally or parenterally. Parenteral administration includes especially intravenous and intramuscular administration. Additionally, in a pharmaceutical composition comprising a compound of formula I or a pharmaceutically-acceptable salt thereof, the weight ratio of active ingredient to carrier will normally be in the range from about 1:6 to about 2:1 and preferably from about 1:4 to about 1:1. However, in any given case, the ratio chosen will depend on such factors as the solubility of the active component, the dosage contemplated and the precise route of administration.

For oral use of a neuroleptic agent of this invention, the compound can be administered, for example, in the form of tablets or capsules or as an aqueous solution or suspension- In the case of tablets for oral use, carriers which can be used include lactose and corn starch, and lubricating agents such as magnesium stearate can be added. For oral administration in capsule form, useful diluents are lactose and dried corn starch. When aqueous suspensions are required for oral use, the active ingredient can be combined with emulsifying and suspending agents. If desired, certain sweetening and or flavoring agents can be added. For intramuscular and intravenous use, sterile solutions of the active ingredient can be prepared and the pH of the solutions should be suitably adjusted and buffered. For intravenous use the total concentration of solutes should be controlled to render the preparation isotonic.

When a neuroleptic agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances an effective amount for treating a psychotic disorder will be a daily dosage in the range from about 3 mg to about 600 mg and preferably from about 30 mg to about 60 mg in single or divided doses, orally or parenterally. In some instances, it may be necessary to use dosages outside these limits.

The present invention is illustrated by the following examples, but is not limited to the details thereof.

The title compounds of examples 37 through 55 are compounds of this invention. The title compounds of examples 1 through 18 are compounds of the formula III above. The title compounds of examples 19 through 36 are compounds of the formula IV above. The title compounds of examples 56 through 69 are compounds of the formula II above.

EXAMPLE 1

6-(Chloroacetyl)-1,2,3,4-tetrahydro-2(1H)-quinolinone ($C_{11}H_1ClNO_2$)

Under nitrogen a mixture of 5.2 ml (0.065 mol) chloroacetyl chloride and 41.4 g (0.31 mol) aluminum trichloride in 200 ml carbon disulfide was stirred while adding 7.36 g (0.05 mol) 1,2,3,4-tetrahydro-2(1H)-quinolinone over a 5 minute period. After a further 15 minute period, the mixture was refluxed for 2 hours, treated with another 20 ml (0.25 mol) chloroacetyl chloride and refluxed another 3 hours. The reaction mixture was cooled to 25° C., the carbon disulfide was decanted and the viscous brown oil was poured cautiously over 500 g ice/water. After stirring for 30 minutes, the precipitated solids were filtered, washed well with water and air dried to give 10.75 g of an off-white solid, (96%), m.p. 215°–218° C. (dec.); MS (%) 223(9), 174(100), NMR ($\delta$, DMSO-d$_6$) 2.0–2.35 (m,2H), 2.45–2.8 (m,2H), 4.7 (s,2H), 6.6 (d,1H), 7.4–7.6 (m,2H), 10.0 (br s,1H).

The 6-chloroacetyl-1,2,3,4-tetrahydro-2(1H)-quinolinones of Examples 2–16 were prepared by a procedure similar to that of Example 1.

EXAMPLE 2

1-Ethyl-6-chloroacetyl-1,2,3,4-tetrahydro-2(1H)-quinolinone $C_{13}H_{14}ClNO_2$, 98%, m.p. 158°–161° C.

EXAMPLE 3

4(R,S)-Methyl-6-chloroacetyl-1,2,3,4-tetrahydro-2(1H)-quinolinone $C_{12}H_{12}ClNO_2$, 48%, m.p. 183°–184° C.

EXAMPLE 4

4R-Methyl-6-chloroacetyl-1,2,3,4-tetrahydro-2(1H)-quinolinone $C_{12}H_{12}ClNO_2$, 87%, m.p. 187°–190° C., $[\alpha]^{25}D+2.1°$ (C=1, acetone).

EXAMPLE 5

4S-Methyl-6-chloroacetyl-1,2,3,4-tetrahydro-2(1H)-quinolinone $C_{12}H_{12}ClNO_2$, 92%, m.p. 187°–190° C., $[\alpha]^{25}D-5.9°$ (C=1, acetone).

EXAMPLE 6

3-Methyl-6-chloroacetyl-1,2,3,4-tetrahydro-2(1H)-quinolinone $C_{12}H_{12}ClNO_2$, 96%, m.p. 216°–221° C.

EXAMPLE 7

7-Methyl-6-chloroacetyl-1,2,3,4-tetrahydro-2(1H)-quinolinone $C_{12}H_{12}ClNO_2$, 91%, m.p. 196°–199° C.

EXAMPLE 8

3,3-Dimethyl-6-chloroacetyl-1,2,3,4-tetrahydro-2(1H)-quinolinone $C_{13}H_{14}ClNO_2$, 97%, m.p. 204°–206° C.

EXAMPLE 9

4,4-Dimethyl-6-chloroacetyl-1,2,3,4-tetrahydro-2(1H)-quinolinone $C_{13}H_{14}ClNO_2$, 98%, m.p. 175°–177° C.

EXAMPLE 10

4,7-Dimethyl-6-chloroacetyl-1,2,3,4-tetrahydro-2(1H)-quinolinone $C_{13}H_{14}ClNO_2$, 92%, m.p. 184°–186° C.

EXAMPLE 11

1,4-Dimethyl-6-chloroacetyl-1,2,3,4-tetrahydro-2(1H)-quinolinone $C_{13}H_{14}ClNO_2$, 88%, m.p. 122°–124° C.

EXAMPLE 12

1,3,3-Trimethyl-6-chloroacetyl-1,2,3,4-tetrahydro-2-(1H)-quinolinone $C_{14}H_{16}ClNO_2$, 94%, oil.

EXAMPLE 13

4,4,7-Trimethyl-6-chloroacetyl-1,2,3,4-tetrahydro-2-(1H)-quinolinone $C_{14}H_{16}ClNO_2$, 95%, m.p. 176°–179° C.

EXAMPLE 14

7-Chloro-6-chloroacetyl-1,2,3,4-tetrahydro-2(1H)-quinolinone $C_{11}H_9Cl_2NO_2$, 58%, 208°–211° C.

EXAMPLE 15

7-Chloro-4,4-dimethyl-6-chloroacetyl-1,2,3,4-tetrahydro-2(1H)-quinolinone $C_{13}H_{13}Cl_2NO_2$, 57%, m.p. 153°–156° C.

EXAMPLE 16

7-Chloro-1-ethyl-6-chloroacetyl-1,2,3,4-tetrahydro-2-(1H)-quinolinone $C_{13}H_{14}Cl_2NO_2$, 60%, m.p. 109°–111° C.

EXAMPLE 17

6-(3-Chloropropionyl)-1,2,3,4-tetrahydro-4-methyl-2(1H)-quinolinone

The title compound was prepared by a procedure similar to that of Example 1, but replacing chloroacetyl chloride with 3-chloropropionyl chloride.

$C_{13}H_{14}ClNO_2$, 96% m.p. 134°–136° C.

EXAMPLE 18

7-Chloroacetyl-1,2,4,5-tetrahydro-2H-1-benzazepin-2-one

The title compound was prepared from 1,3,4,5-tetrahydro-2H-1-benzazepin-2-one by a procedure similar to that of Example 1.

EXAMPLE 19

6-(2-Chloroethyl)-1,2,3,4-tetrahydro-2(1H)-quinolinone

Under nitrogen, a mixture of 6.71 g of the title compound of Example 1 and 23 ml (0.30 mol) trifluoroacetic acid was treated dropwise with 11.0 ml (0.069 tool) triethylsilane. After 72 hours at 25° C. the dark brown solution was poured slowly over 200 ml ice, stirred for 30 minutes and filtered. The solids were washed well with water and dried to give a tan colored product, 5.42 g (86%), m.p. 148°–153° C. (dec.); MS(%) 211 (10), 209 (34), 160 (100), 132 (45); NMR ($\delta$, DMSO-$d_6$) 2.0–2.3 (m,2H), 2.4–2.75 (m,4H), 3.4 (t,2H), 6.40 (d, 1H), 6.6–6.8 (m, 2H), 9.7 (br s, 1H).

By a process similar to that of example 19, the following "R" substituted 6-(2-chloroethyl)-1,2,3,4-tetrahydro-2(1H)-quinolinones of examples 20 through 34 were prepared.

| Example | "R" | Molecular Formula | m.p. °C. | Yield % | MS (%)/ $[\alpha]^{25}D$ |
|---|---|---|---|---|---|
| 20 | 1-ethyl | $C_{13}H_{16}ClNO$ | 55–58 | 94 | |
| 21 | 4(R,S)-methyl | $C_{12}H_{14}ClNO$ | 176–178 | 87 | |
| 22 | 4R-methyl | $C_{12}H_{14}ClNO$ | 176–178 | 84 | /+ 8.9° c = 1, acetone |
| 23 | 4S-methyl | $C_{12}H_{14}ClNO$ | 176–178 | 88 | /− 8.5° c = 1, acetone |
| 24 | 3-methyl | $C_{12}H_{14}ClNO$ | 136–140 | 70 | |
| 25 | 7-methyl | $C_{12}H_{14}ClNO$ | 233–234 | 57 | |
| 26 | 3,3-dimethyl | $C_{13}H_{16}ClNO$ | 136–138 | 78 | |
| 27 | 4,4-dimethyl | $C_{13}H_{16}ClNO$ | 175–178 | 61 | |
| 28 | 4,7-dimethyl | $C_{13}H_{16}ClNO$ | 178–180 | 69 | |
| 29 | 1,4-dimethyl | $C_{13}H_{16}ClNO$ | 77–79 | 83 | |
| 30 | 1,3,3-trimethyl | $C_{14}H_{18}ClNO$ | Oil | 84 | 251(77), 202(100)/ |
| 31 | 4,4,7-trimethyl | $C_{14}H_{18}ClNO$ | 203–207 | 86 | |
| 32 | 7-chloro | $C_{11}C_{11}Cl_2NO$ | 238–240 | 63 | |
| 33 | 7-chloro-4,4-dimethyl | $C_{13}H_{15}Cl_2NO$ | 194–196 | 85 | |
| 34 | 7-chloro-1-ethyl | $C_{13}H_{15}Cl_2NO$ | 94–97 | 52 | |

EXAMPLE 35

6-(3-chloropropyl)-1,2,3,4-tetrahydro-4-methyl-2(1H)-quinolinone

Using a procedure similar to that of Example 19, the title compound was prepared by reducing 6-(3-chloropropionyl)-1,2,3,4-tetrahydro-4-methyl-2(1H)-quinolinone, $C_{13}H_{16}ClNO$, 70%, m.p.92°–94° C.

EXAMPLE 36

7-(2-Chloroethyl)-1,3,4,5-tetrahydro-2H-1-benzazepin-2-one

Using a procedure similar to that of Example 19, the title compound was prepared by reducing 7-chloroacetyl-1,3,4,5-tetrahydro-2H-1-benzazepin-2-one, $C_{12}H_{14}ClNO$, oil, 83%.

EXAMPLE 37

6-(2-(4-(1,2-benzisothiazol-3-yl)piperazinyl)ethyl-1,2,3,4-tetrahydro-2(1H)-quinolinone hydrochloride hemihydrate Under nitrogen a mixture of 1.097 g (5.0 mmol) 1-(1,2-benzisothiazol-3-yl)piperazine, 1.05 g (5.0 mmol) 6-(2-chloroethyl) -1,2,3,4-tetrahydro-2(1H)-quinolinone, 1.06 g (10.0 mmol) sodium carbonate, 0.083 g (0.5 retool) potassium iodide and 35 ml methyl isobutyl ketone (MIBK) was heated at 90° C. for 18 hours. After cooling to 25° C., the mixture was filtered, the solids were washed with another 100 ml MIBK and the combined filtrates were concentrated in vacuo to an orange solid. After chromatography on silica gel (230–400 mesh, 45×160 mm), eluting with ethyl acetate, the product fractions were combined and concentrated in vacuo, diluted in 15 ml methylene dichloride and treated with hydrogen chloride saturated ethyl ether to give a pale yellow solid, 0.280 g (13%), m.p. 285°–288° C.; MS(%) 392(1), 232(100), 177, 160; Anal. for $C_{22}H_{24}N_4OS \cdot HCl \cdot \frac{1}{2}H_2O$: C 60.33, H 5.98, N 12.79. Found: C 59.98, B 5.84, N 12.66.

Using a procedure similar to that of Example 37, the 6-(2-(4-(1,2-benzisothiazol-3-yl)piperazinyl)ethyl)-1,-2,3,4-tetrahydro-2(1H)-quinolinones of examples 38–52 were prepared.

EXAMPLE 38

1-Ethyl-6-(2-(4-(1,2-benzisothiazol-3-yl)piperazinyl)ethyl)-1,2,3,4tetrahydro-2(1H)-quinolinone 70%, m.p. 94° C., MS (%): 420 (1), 232 (100).

EXAMPLE 39

4(R,S)-Methyl-6-(2-(4-(1,2-benzisothiazol-3-yl)piperazinyl)ethyl)-1,2,3,4 tetrahydro-2(1H)-quinolinone 37%, m.p. 241°–243° C., Anal. for $C_{23}H_{26}N_4OS \cdot HCl \cdot H_2O$: C, 59.92, H, 6.34, N, 12.15. Found: C, 59.87, H, 6.39, N, 11.88.

EXAMPLE 40

4R-Methyl-6-(2-(4-(1,2-benzisothiazol-3-yl)piperazinyl)ethyl)-1,2,3,4 tetrahydro-2(1H)-quinolinone 77%, m.p. 246° C.; Anal. for $C_{23}H_{26}N_4OS \cdot HCl \cdot H_2O$: C, 59.92, B, 6.34, N, 12.15. Found: C, 60.24, H, 6.27, N, 11.88.

EXAMPLE 41

4S-Methyl-6-(2-(4-(1,2-benzisothiazol-3-yl)piperazinyl)ethyl)-1,2,3,4 tetrahydro-2(1H)-quinolinone 78%, m.p. 246°–248° C.; Anal. for $C_{23}H_{26}N_4OS \cdot HCl \cdot H_2O$: C, 59.92, H, 6.34, N, 12.15. Found: C, 59.66, H, 6.45, N, 11.78.

EXAMPLE 42

3-Methyl-6-(2-(4-(1,2-benzisothiazol-3-yl)piperazinyl)ethyl)-1,2,3,4 tetrahydro-2(1H)-quinolinone 59%, m.p. 190°–192° C.; Anal. for $C_{23}H_{26}N_4OS$: C, 67.95, H, 6.45, N, 13.78. Found: C, 67.73, H, 6.47, N, 13.33.

EXAMPLE 43

7-Methyl-6-(2-(4-(1,2-benzisothiazol-3-yl)piperazinyl)ethyl)-1,2,3,4tetrahydro-2(1H)-quinolinone 24%, m.p. 200° C. (dec.); Anal. for $C_{23}H_{26}N_4OS.\frac{1}{2}$ $H_2O$: C, 66.48, H, 6.55, N, 13.48. Found: C, 66.88, H, 6.33, N, 13.45.

EXAMPLE 44

3,3-Dimethyl-6-(2-(4-(1,2-benzisothiazol-3-yl)-piperazinyl)ethyl)-1,2,3,4 tetrahydro-2(1H)-quinolinone 59%, m.p. 195°-198° C.; Anal. for $C_{24}H_{28}N_4OS.\frac{1}{2}$ $H_2O$: C, 67.10, H, 6.80, N, 13.04. Found: C, 66.92, H, 6.75, N, 12.81.

EXAMPLE 45

4,4-Dimethyl-6-(2-(4-(1,2-benzisothiazol-3-yl)-piperazinyl)ethyl)-1,2,3,4 tetrahydro-2(1H)-quinolinone 78%, m.p. 264° C. (dec.); Anal. for $C_{24}H_{28}N_4OS.HCl.H_2O$: C, 60.68, H, 6.58, N, 11.79. Found: C, 60.33, H, 6.35, N, 11.47;

EXAMPLE 46

4,7-Dimethyl-6-(2-(4-(1,2-benzisothiazol-3-yl)piperazinyl)ethyl)-1,2,3,4 tetrahydro-2(1H)-quinolinone 38%, m.p. 189°-191° C.; Anal. for $C_{24}H_{28}N_4OS.\frac{1}{2}$ $H_2O$: C, 67.81, H, 6.76, N, 13.18. Found: C, 67.98, H, 6.78, N, 13.01;

EXAMPLE 47

1,4-Dimethyl-6-(2-(4-(1,2-benzisothiazol-3-yl)piperazinyl)ethyl)-1,2,3,4 tetrahydro-2(1H)-quinolinone 47%, m.p. 251°-252° C. (dec.); Anal. for $C_{24}H_{28}N_4OS.HCl$: C, 63.01, H, 6.40, N, 12.26. Found: C, 62.65, H, 6.24, N, 11.87.

EXAMPLE 48

1,3,3-Trimethyl-6-(2-(4-(1,2-benzisothiazol-3-yl)piperazinyl)ethyl)-1,2,3,4 tetrahydro-2(1H)-quinolinone 44%, m.p. 259°-263° C.; Anal. for $C_{25}H_{30}N_4OS.HCl.\frac{1}{3}H_2O$: C, 62.94, H, 6.69, N, 11.74. Found: C, 62.95, H, 6.51, N, 11.60.

EXAMPLE 49

4,4,7-Trimethyl-6-(2-(4-(1,2-benzisothiazol-3-yl)-piperazinyl)ethyl)-1,2,3,4 tetrahydro-2(1H)-quinolinone 56%, m.p. 257° C. (dec.); Anal. for $C_{25}H_{30}N_4OS.HCl$: C, 61.39, H, 6.80, N, 11.46. Found: C, 61.59, H, 6.61, N, 11.10.

EXAMPLE 50

7-Chloro-6-(2-(4-(1,2-benzisothiazol-3-yl)piperazinyl)ethyl)-1,2,3,4 tetrahydro-2(1H)-quinolinone 52%, m.p. 212°-215° C.; Anal. for $C_{22}H_{23}ClN_4OS.\frac{1}{4}$ $H_2O$: C, 61.24, H, 5.49, N, 12.99. Found: C, 61.30, H, 5.43, N, 12.72.

EXAMPLE 51

7-Chloro-4,4-dimethyl-6-(2-(4-(1,2-benzisothiazol-3-yl)piperazinyl)ethyl)-1,2,3,4 tetrahydro-2(1H)-quinolinone 56%, m.p. 290°-292° C.; Anal. for $C_{24}H_{27}ClN_4OS.HCl$: C, 58.65, H, 5.74, N, 11.40. Found: C, 58.29, H, 5.69, N, 11.25.

EXAMPLE 52

7-Chloro-1-ethyl-6-(2-(4-(1,2-benzisothiazol-3-yl)piperazinyl)ethyl)-1,2,3,4 tetrahydro-2(1H)-quinolinone 61%, m.p. 281° C. (dec.); Anal. for $C_{24}H_{27}ClN_4OS.HCl.\frac{1}{4}H_2O$: C, 58.12, H, 5.79, N, 11.30. Found: C, 58.06, H, 5.63, N, 10.97.

EXAMPLE 53

6-(3-(4-(1,2-Benzisothiazol-3-yl)-piperazinyl)propyl)-1,2,3,4-tetrahydro-4-methyl-2(1H)-quinolinone The title compound was prepared in manner similar to that of Example 37. 79%, m.p. 156°-157° C., Anal. for $C_{24}H_{28}N_4OS$: C, 68.54, H, 6.71, N, 13.32. Found: C, 68.36, H, 6.64, N, 13.30.

EXAMPLE 54

7-(2-(4-(1,2-Benzisothiazol-3yl)-piperazinyl)ethyl)-1,3,4,5-tetrahydro-2H-1-benzazepin-2-one The title compound was prepared by a procedure similar to that of Example 37. 23%, m.p. 173°-174.5° C.

EXAMPLE 55

7-(2-(4-(1,2-Benzisothiazol-3-yl)piperazinyl)ethyl)-1,3,4,5-tetrahydro-1-methyl-2H-1-benzazepin-2-one Under nitrogen, sodium hydride (20 mg, 0.5 mmol, 60% oil dispersed) was washed free of oil with pentane and layered with 6 ml dimethylformamide. In one portion, 155 mg (0.38 mmol) 7-(2-(4-(1,2-benzisothiazol-3-yl)piperazinyl)ethyl)-1,3,4,5-tetrahydro-2H-1-benzazepin-2-one (the title compound of Example 54) was added and stirring was continued for 0.5 hours at 25° C. To the solution was then added methyl iodide (162 mg, 1.14 mmol) and stirring was continued overnight. After pouring over 60 ml ice/water, the product was extracted with 40 ml ethyl acetate which was washed with water (2×50 ml), dried with sodium sulfate and concentrated to an oil, 54 mg. Chromatography (32–63 micron silica gel) eluting with 2% methanol in methylene dichloride provided the pure free base, 46 mg (29%).

EXAMPLE 56

1,2,3,4-Tetrahydro-4(R,S)-methyl-2(1H)-quinolinone

The title compound was prepared according to the method of R. Brettle and S. M. Shibib, J. Chem. Soc., Part I, 2912-2919, (1981). Thus, 2-hydroxy-4-methylquinoline (Aldrich) in methanol was reduced with magnesium metal, white solid, 47%, m.p. 98°-101° C. (lit. m.p. 97°-98° C.).

EXAMPLE 57

4,7-Dimethyl-1,2,3,4-tetrahydro-4(R,S)-methyl-(2(1H)-quinoline

The title compound was prepared in a manner similar to that of Example 56, m.p. 117°-118.5° C., 42%, MS (%): 175 (60, M+), 160 (100).

According to the procedure of A. Kraska et al., European Patent Application 0130795, the "R" substituted 1,2,3,4-tetrahydro-2(1H)-quinolinones of Examples 58-60 were prepared:

| Example | "R" | m.p. (°C.) | Yield (%) |
|---|---|---|---|
| 58 | 4,4-dimethyl | 97–101 | 85 |
| 59 | 4,4,7-trimethyl | 115–118 | 34 |
| 60 | 7-chloro-4,4-dimethyl | 168–171 | 50 |

According to the method of D. W. Robertson, et al (J. Med. Chem., 29 (10) 1832-1840 (1986), 1,2,3,4-tetrahydro-2 (1H)-quinolinone (dihydrocarbostyril) was converted to the "R" substituted 1,2,3,4-tetrahydro-2(1H)-quinolinones of Examples 61–62.

| Example | "R" | m.p. (°C.) | Yield (%) | NMR |
|---|---|---|---|---|
| 61 | 3,3-dimethyl | 154–156 | 49 | |
| 62 | 1,3,3-trimethyl | Oil | 44 | $^1$H-NMR (300 MHz, $\delta$, CDCl$_3$): 1.15 (S, 6H), 2.7 (s, 2H), 3.35 (s, 3H), 6.9 (d, 1H), 7.0 (t, 1H), 7.1 (d, 1H), 7.2 (t, 1H) |

EXAMPLE 63

7-Chloro-1,2,3,4-tetrahydro-2(1H)-quinolinone

To a solution of 6.58 g (28.9 mmole) of 4-chloro-2-nitrocinnamic acid (prepared according to the method of G. R. Pettit and A. B. Neill, Can. J. Chem., 42, 1764–1768 (1964)), in 150 ml ethanol and 4 ml acetic acid was added 1 level teaspoon of Raney nickel and the mixture was hydrogenated at 40–50 psi/25° C. for 3 hours. The mixture was filtered through a pad of diatomaceous earth and the filtrate was concentrated to a crude solid. This solid was triturated with ethyl acetate and filtered to give the product as a white solid, 4.06 g (77%, m.p. 184°–186° C., MS(%): 183(33, M+2), 181(100, M+).

EXAMPLE 64

7-Methyl-1,2,3,4-tetrahydro-2(1H)-quinolinone

The title compound was prepaed according to the method of T. Kametani, H. Nemoto and S. Takano, Chem. Pharm. Bull., 16 (2), 367-370 (1968) m.p. 158°-160° C. (lit. m.p. 160°-161° C.).

EXAMPLE 65

1-Ethyl-1,2,3,4-tetrahydro-2(1H)-quinolinone

The title compound was prepared by stirring 11.3 mmol of 1,2,3,4-tetrahydro-2(1H)-quinolinone in 85 ml dry dimethylformamide with 12.1 mmol potassium tert-butoxide for two hours at 25° C., then adding 12.1 mmol ethyl iodide and refluxing for 20 hours. The product was isolated by pouring the reaction mixture over ice/water (about 200 ml), stirring until the ice melted, extracting with diethyl ether and drying the organic extracts over magnesium sulfate. The residue obtained on concentrating the organics was chromatographed (230–400 mesh silica gel, 75% hexane: 25% ethyl acetate). The product obtained was an oil, 56%.

EXAMPLE 66

7-Chloro-1-ethyl-1,2,3,4-tetrahydro-2(1H)-quinolinone

The title compound was prepared in a manner similar to Example 65, but using 7-chloro-1,2,3,4-tetrahydro-2(1H)-quinolinone (the title compound of Example 63) instead of 1,2,3,4-tetrahydro-2(1H)-quinolinone. The product obtained was an oil, 28%.

EXAMPLE 67

1,4-Dimethyl-1,2,3,4-tetrahydro-2(1H)-quinolinone

The title compound was prepared from 1,2,3,4-tetrahydro-4(R,S)-methyl-2(1H)-quinolinone in a manner similar to that of Example 65, but using methyl iodide instead of ethyl iodide and using potassium tert-butoxide as the base. The product so obtained was an oil (52%, MS(%): 175(100 M+) 160(95), 132(87)).

EXAMPLE 68

4(S)-Methyl-1,2,3,4-tetrahydro-2(1H)-quinolinone 3-phenylbutyric acid (Aldrich Chem Co.) was resolved according to the method of A. Weidler and G. Bergson (Acta Chem. Scand., 1964, 18 (6), 1484–1486) into the corresponding enantiomers: 3S-(+)-phenylbutyric acid (oil, $[\alpha]^{25}$D +50.7° (c=1, benzene)) and 3R-(−)-phenylbutyric acid (oil, $[\alpha]^{25}$D −49.4° (c=1, benzene)).

Polyphosphoric acid (132 g, Aldrich) was preheated to 100° C. in an open beaker and 3 (S)-(+)-phenylbutyric acid (13.2 g, 80.4 mmol) was added. After 3 hours of mechanical stirring at 100° C. the mixture was cooled to approximately 50° C. and poured over 600 ml ice/water. The resulting oil was extracted with ethyl acetate, dried over magnesium sulfate and concentrated to a dark orange oil, 11.2 g. Distillation at 94° C./1.3 mm mercury gave pure 3(S)-methyl-1-indanone (6.77 g, 58%, $[\alpha]^{25}$D+15.9° (c=1, acetone)), as reported by H. J. Hansen, Helv. Chem. Acta, 1979, 62 (4), 1120–1128. In the same way, cyclization of 3R-(−)-phenylbutyric acid (14.9 g) in 149 g polyphosphoric acid gave, after distillation, pure 3R-methyl-1-indanone (9.52 g, 72% , $[\alpha]^{25}$D −16.7° (c=1, acetone)).

According to a procedure in J. Org. Chem., 1958, 23, 1330, 3(S)-(+)-methyl-1-indanone (6.7 g, 45.8 mmol) in 100 g polyphosphoric acid was treated with sodium azide (3.12 g, 48.1 mmol) in small portions over a 30 minute period, then heated to 50° C. with continued mechanical stirring overnight. The yellow viscous reaction mixture was cooled to 25° C., poured over 600 ml ice/water and made alkaline with 2 normal sodium hydroxide (to pH 8–9). This was extracted with methylene dichloride, the organics were washed with saturated sodium bicarbonate and sodium chloride, and finally dried with magnesium sulfate and concentrated to a residue, 6.7 g. Chromatography (230–400 silica gel, 60% hexane: 40% ethyl acetate) provided pure 4(S)-methyl-1,2,3,4-tetrahydro-2(1H)-quinolinone as a white solid, 3.2 g (43%, m.p. 92°–94° C., $[\alpha]^{25}$D −38.8° (c=1, acetone).

EXAMPLE 69

4(R)-Methyl-1,2,3,4-tetrahydro-2(1H)-quinolinone

The title compound was prepared in a manner similar to that of Example 68, m.p. 93°–96° C., $[\alpha]^{25}D$ +36.9°, (c=1, acetone).

I claim:

1. A compound having the formula

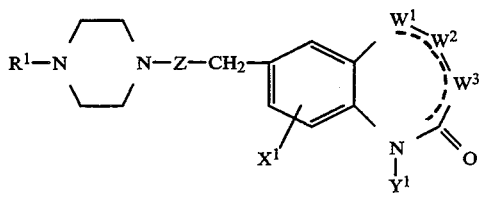

wherein $W^1$ is $CR^2R^3$, $W^2$ is $CR^4R^5$, $W^3$ is $CR^6R^7$, and one of $W^1$, $W^2$ and $W^3$ may be absent, and wherein the broken line extending from $W^1$ to $W^3$ represents an optional double bond between either $W^1$ and $W^2$ or $W^2$ and $W^3$, in which case two of $R^2$, $R^3$, $R^4$, $R^5$, $R^6$ and $R^7$ are absent; and wherein $X^1$ is hydrogen, halogen ($C_1$–$C_4$) alkyl, ($C_1$–$C_4$) alkoxy, nitro, cyano, trifluoromethyl, or pentafluoroethyl; $Y^1$ is hydrogen, ($C_1$–$C_4$) alkyl, phenyl or substituted phenyl, wherein said substituted phenyl is substituted with one or more substituents that are independently selected from the group consisting of halogen, ($C_1$–$C_4$) alkyl, ($C_1$–$C_4$) alkoxy, nitro, cyano, trifluoromethyl or pentafluoroethyl, or when $X^1$ is attached to the carbon atom ortho to the carbon atom to which N-$Y^1$ is attached then $X^1$ and $Y^6$ together may optionally form a saturated heterocyclic ring selected from pyrrolidine, piperidine, perhydroazepine, 3-oxazolane and morpholine;

$R^1$ is

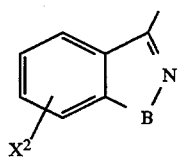

wherein B is selected from the group consisting of S, O and $NY^2$; $X^2$ is hydrogen, halogen, ($C_1$–$C_4$) alkyl, ($C_1$–$C_4$) alkoxy, nitro, cyano, trifluoromethyl or pentafluoroethyl; $Y^2$ is hydrogen, ($C_1$–$C_4$) alkyl, phenyl or substituted phenyl, wherein said substituted phenyl is substituted with one or more substituents that are independently selected from the group consisting of halogen, ($C_1$–$C_4$) alkyl, ($C_1$–$C_4$) alkoxy, nitro, cyano, trifluoromethyl or trifluoroethyl; $R^2$, $R^3$, $R^4$, $R^5$, $R^6$ and $R^7$ are independently selected from the group consisting of hydrogen and lower alkyl, or any two of $R^2$, $R^3$, $R^4$, $R^5$, $R^6$ and $R^7$ taken together with the carbon or carbons to which they are attached form a ($C_3$–$C_7$) saturated or unsaturated carbocyclic ring; and Z is ($C_1$–$C_6$) alkyl, branched ($C_1$–$C_6$) alkyl, ($C_1$–$C_6$) alkenyl or branched ($C_1$–$C_6$) alkenyl, and the pharmaceutically acceptable salts thereof.

2. A compound according to claim 1, with the proviso that when $Y^1$ is hydrogen and $W^3$ is absent, then the heterocyclic ring carbons of $W^1$ and $W^2$ are connected by a carbon-carbon single bond.

3. A compound according to claim 1, wherein $Y^1$ is hydrogen, $W^3$ is absent and the heterocyclic ring carbons of $W^1$ and $W^2$ are connected by a carbon-carbon double bond.

4. A compound according to claim 1, said compound being selected from the group consisting of:
   6-(2-(4-(1,2-benzisothiazol-3-yl)piperazinyl)ethyl)-1,2,3,4-tetrahydro-2(1H)-quinolinone hydrochloride hemihydrate,
   4(R,S)-methyl-6-(2-(4-(1,2-benzisothiazol-3-yl)piperazinyl)ethyl)-1,2,3,4-tetrahydro-2(1H)-quinolinone hydrochloride hydrate,
   4S-methyl-6-(2-(4-(1,2-benzisothiazol-3-yl)piperazinyl)ethyl)-1,2,3,4-tetrahydro-2(1H)-quinolinone hydrochloride hydrate,
   4R-methyl-6-(2-(4-(1,2-benzisothiazol-3-yl)piperazinyl)ethyl)-1,2,3,4 -tetrahydro-2(1H)-quinolinone hydrochloride hydrate,
   7-chloro-6-(2-(4-(1,2-benzisothiazol-3-yl)piperazinyl)ethyl)-1,2,3,4-tetrahydro-2(1H)-quinolinone quarterhydrate,
   6-(3-(4-(1,2-benzisothiazol-3-yl)piperazinyl)propyl)-1,2,3,4-tetrahydro-4-methyl-2(1H)-quinolinone,
   7-(2-(4-(1,2-benzisothiazol-3-yl)-piperazinyl)ethyl)-1,3,4,5-tetrahydro-2H-1-benzazepin-2-one,
   1-ethyl-6-(2-(4-(1,2-benzisothiazol-3-yl)piperazinyl)ethyl)-1,2,3,4-tetrahydro-2(1H)-quinolinone, and
   4,4-dimethyl-6-(2-(4-(1,2-benzisothiazol-3-yl)piperazinyl)ethyl)-1,2,3,4-tetrahydro-2(1H)-quinoline.

5. A pharmaceutical composition for the treatment or prevention of psychosis and anxiety, comprising an amount of a compound according to claim 1 effective in treating or preventing psychosis or anxiety.

6. A method for the treatment or prevention of psychosis or anxiety, comprising administering to a person in need of said treatment or prevention a compound according to claim 1 in an amount effective to treat or prevent psychosis or anxiety.

* * * * *